(12) United States Patent
Milne et al.

(10) Patent No.: US 6,703,467 B1
(45) Date of Patent: Mar. 9, 2004

(54) ADHESIVES AND SEALANTS

(75) Inventors: Paul E Milne, Malvern (GB); Keith M Blackwood, Malvern (GB); Alan W Hall, Hull (GB); John W Goodby, Hull (GB)

(73) Assignee: Qinetiq Limited, Hants (GB)

( * ) Notice: Subject to any disclaimer, the term of this patent is extended or adjusted under 35 U.S.C. 154(b) by 0 days.

(21) Appl. No.: 09/720,990

(22) PCT Filed: Jul. 26, 1999

(86) PCT No.: PCT/GB99/02432
§ 371 (c)(1),
(2), (4) Date: Jan. 3, 2001

(87) PCT Pub. No.: WO00/06658
PCT Pub. Date: Feb. 10, 2000

(30) Foreign Application Priority Data

Jul. 25, 1998  (GB) ............................................... 9816169

(51) Int. Cl.$^7$ .......................... C08F 20/54; C08F 226/04
(52) U.S. Cl. .................... 526/303.1; 526/305; 526/306; 526/310; 526/312
(58) Field of Search .............................. 526/303.1, 305, 526/306, 310, 312

(56) References Cited

U.S. PATENT DOCUMENTS

| | | | |
|---|---|---|---|
| 3,888,928 A | | 6/1975 | Lang et al. |
| 3,912,693 A | | 10/1975 | Shimizu et al. |
| 4,121,986 A | | 10/1978 | Battaerd |
| 4,988,753 A | | 1/1991 | Rullmann et al. |
| 6,388,037 B2 | * | 5/2002 | Schultz et al. .............. 526/305 |

FOREIGN PATENT DOCUMENTS

| | | |
|---|---|---|
| DE | 18 14 597 | 7/1969 |
| EP | 0 969 028 A2 | 1/2000 |
| EP | 0 969 061 A2 | 1/2000 |
| EP | 0970 946 A2 | 1/2000 |
| FR | 2 109 692 | 3/1972 |
| WO | 97/42550 | 11/1997 |

OTHER PUBLICATIONS

Marek, Miroslav, Jr. et al.: "Preparation of a multilayered film of ultrathin poly(tetraallylammonium bromide) network" Chem. Lett. (1933), 2 291–4, p. 292, paragraphs 1–3.

G. C. Fu et al.: "Catalytic ring–closure metathesis of functionalized dienes by a ruthenium carbene complex" Journal of the American Chemical Society, vol. 115, 1993, pp. 9856–9857, DC US, p. 9857.

G. B. Butler et al.: "Preparation of Polymerization of unsaturated Quaternary Ammonium Compounds. VII. Derivatives of 1, x–diamino–alkanes" Journal of the American Chemical Society., vol. 78, 1956, pp. 4797–4800, DC US, p. 4799.

* cited by examiner

Primary Examiner—Robert Deshon Harlan
(74) Attorney, Agent, or Firm—Nixon & Vanderhye P.C.

(57) ABSTRACT

An adhesive or sealant composition comprising a compound of formula (I) provided that at least one of (a) $R^1$ and $R^6$ or (b) $R^2$ and $R^3$ or (c) $R^4$ and $R^5$ includes an electron withdrawing group; and where necessary, a polymerization initiator. Novel compounds of formula (I) are also described and claimed. Adhesive compositions can be used to bond for example glass and metal surfaces. Certain biocompatible adhesives for medical applications are included.

28 Claims, 1 Drawing Sheet

ADHESIVES AND SEALANTS

Figure 1:
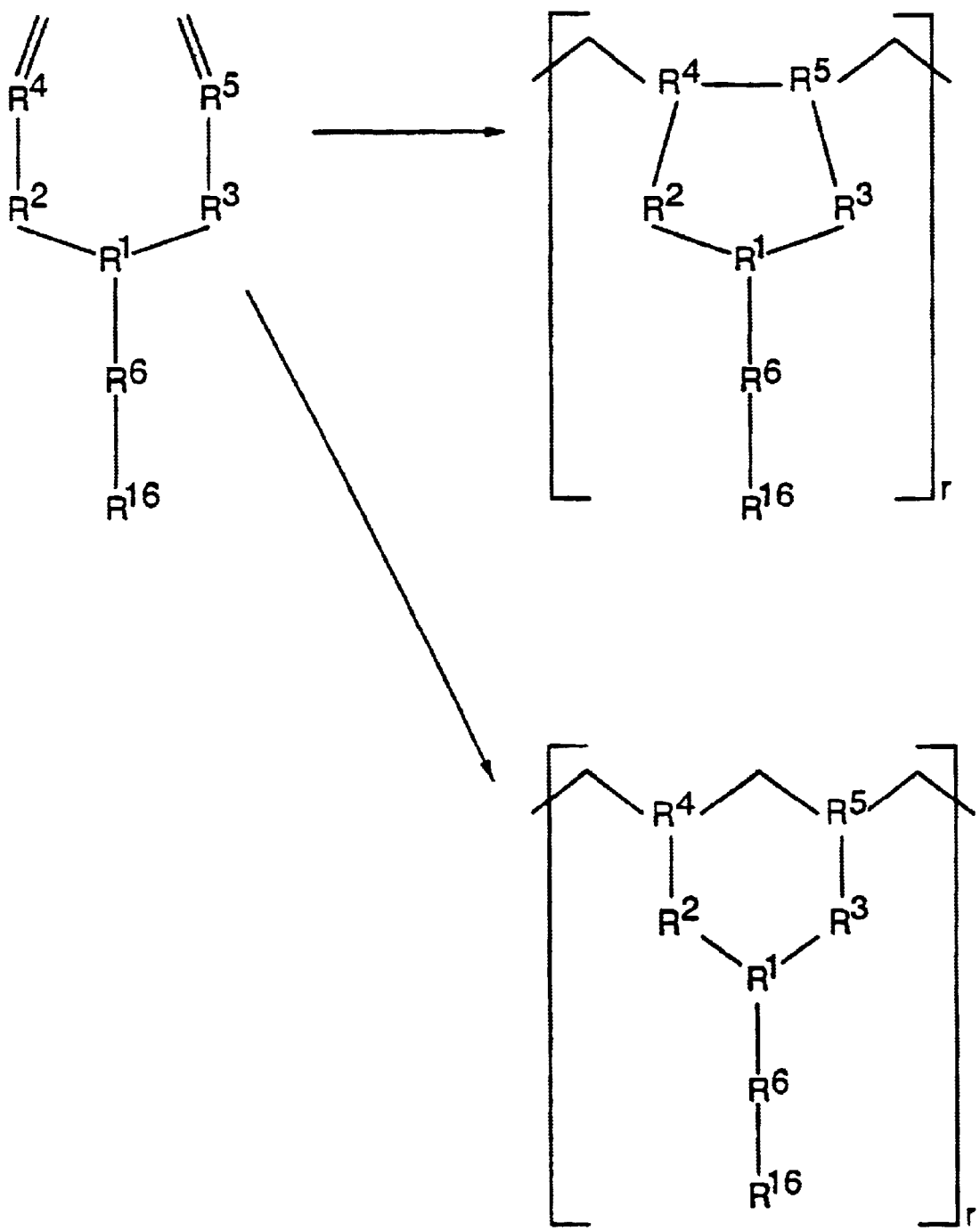

The present invention relates to adhesive and/or sealant compositions, to novel compounds which may be used in the compositions and to methods of their production.

The applicants have found that certain unsaturated monomeric compounds can, under particular conditions, polymerise so as to form effective adhesion between surfaces.

According to the present invention there is provided an adhesive or sealant composition comprising a compound of formula (I)

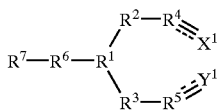

where
- $R^1$ is CH and $R^6$ is a bond, or $R^1$ and $R^6$ together form an electron withdrawing group;
- $R^2$ and $R^3$ are independently selected from $(CR^{8'}R^8)_n$, or a group $CR^9R^{10}$, $-(CR^{8'}R^6CR^9R^{10})-$ or $-(CR^9R^{10}CR^{8'}R^8)-$ where n is 0, 1 or 2, $R^{8'}$ and $R^8$ are independently selected from hydrogen or alkyl, and either one of $R^9$ or $R^{10}$ is hydrogen and the other is an electron withdrawing group, or $R^9$ and $R^{10}$ together form an electron withdrawing group,
- $R^4$ and $R^5$ are independently selected from CH or $CR^{11}$ where $R^{11}$ is an electron withdrawing group, and
- $R^7$ is hydrogen, an optionally substituted hydrocarbyl group, a perhaloalkyl group or a functional group;
- the dotted lines indicate the presence or absence of a bond,
- and $X^1$ is a group $CX^2X^3$ where the dotted line bond to which it is attached is absent and a group $CX^2$ where the dotted line bond to which it is attached is present, $Y^1$ is a group $CY^2Y^3$ where the dotted line bond to which it is attached is absent and a group $CY^2$ where the dotted line bond to which it is attached is present, and $X^2$, $X^3$, $Y^2$ and $Y^3$ are independently selected from hydrogen and fluorine;
- provided that at least one of (a) $R^1$ and $R^6$ or (b) $R^2$ and $R^3$ or (c) $R^4$ and $R^5$ includes an electron withdrawing group;
- and where necessary, a polymerization initiator.

As used herein, the expression "adhesive or sealant composition" includes either an adhesive composition and/or a sealant composition. An "adhesive composition" is a glue—like material which, when interposed between surfaces, will hold the surfaces together. The resulting bond between the surface is sufficiently strong and will remain in place for a period of time which is appropriate for the desired application. Surfaces include glass, metal, wood, paper, card, ceramics, plastics, laminates, stone, construction materials as well as biological material such as tissue. The expression "sealant composition" refers to compositions which may be applied to one or more surfaces to form a protective barrier thereon, for example to prevent ingress or egress of solid, liquid or gaseous material or alternatively to allow selective permeability through the barrier to gas and/or liquid. In particular, it may provide a seal between surfaces.

Preferably, where $R^2$ and $R^3$ are both $(CR^7R^8)_n$, at least one n is 1 or 2. Suitably in formula (I), n is 1 or 2.

As used herein, the term "alkyl" refers to straight or branched chain alkyl groups, suitably containing up to 20 and preferably up to 6 carbon atoms. The term "alkenyl" and "alkynyl" refer to unsaturated straight or branched chains which include for example from 2–20 carbon atoms, for example from 2 to 6 carbon atoms. Chains may include one or more double or triple bonds respectively. In addition, the term "aryl" refers to aromatic groups such as phenyl or naphthyl.

The term "hydrocarbyl" refers to any structure comprising carbon and hydrogen atoms. For example, these may be alkyl, alkenyl, alkynyl, aryl such as phenyl or napthyl, aralkyl, cycloalkyl, cycloalkenyl or cycloalkynyl. Suitably they will contain up to 20 and preferably up to 10 carbon atoms. The term "heterocyclyl" includes aromatic or non-aromatic rings, for example containing from 4 to 20, suitably from 5 to 10 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, iosquinolinyl, quinoxalinyl, benzthiazolyl, benzoxazolyl, benzothienyl or benzofuryl.

The term "functional group" refers to reactive groups such as halo, cyano, nitro, oxo, $C(O)_nR^a$, $OR^a$, $S(O)_tR^a$, $NR^bR^c$, $OC(O)NR^bR^c$, $C(O)NR^bR^c$, $OC(O)NR^bR^c$, $-NR^7C(O)_nR^6$, $-NR^aCONR^bR^c$, $NR^aCSNR^bR^c$, $-C=NOR^a$, $-N=CR^bR^c$, $S(O)_tNR^bR^c$, $C(S)_nR^a$, $C(S)OR^a$, $C(S)NR^bR^c$ or $-NR^bS(O)_tR^a$ where $R^a$, $R^b$ and $R^c$ are independently selected from hydrogen or optionally substituted hydrocarbyl, or $R^b$ and $R^c$ together form an optionally substituted ring which optionally contains further heteroatoms such as $S(O)_t$, oxygen and nitrogen, n is an integer of 1 or 2, t is 0 or an integer of 1–3. In particular the functional groups are groups such as halo, cyano, nitro, oxo, $C(O)_nR^a$, $OR^a$, $S(O)_tR^a$, $NR^bR^c$, $OC(O)NR^bR^c$, $C(O)NR^bR^c$, $OC(O)NR^bR^c$, $-NR^7C(O)_nR^6$, $-NR^aCONR^bR^c$, $-C=NOR^a$, $-N=CR^bR^c$, $S(O)_tNR^bR^c$, or $-NR^bS(O)_tR^a$ where $R^a$, $R^b$ and $R^c$, n and t are as defined above.

The term "heteroatom" as used herein refers to non-carbon atoms such as oxygen, nitrogen or sulphur atoms. Where the nitrogen atoms are present, they will generally be present as part of an amino residue so that they will be substituted for example by hydrogen or alkyl.

A particular functional group for $R^7$ is an amide. The term "amide" is generally understood to refer to a group of formula $C(O)NR^aR^b$ where $R^a$ and $R^b$ are hydrogen or an optionally substituted hydrocarbyl group.

Suitable *polymerization initiators for inclusion in the compositions of the invention will depend upon the nature of the compound of formula (I) and the intended use to which the adhesive or sealant is to be put. For instance, where an adhesive is intended for use in circumstances where it is or may be exposed to ultraviolet radiation, such as in the adhesion of transparent materials such as glass, the compound of formula (I) is suitably a compound which will polymerise or cure under the influence of u.v. radiation. In such cases, suitable polymerisations initiators will include 2,2'-azobisisobutyronitrile (AIBN) aromatic ketones such as benzophenones in particular acetophenone; chlorinated acetophenones such as di- or tri-chloroacetophenone; dialkoxyacetophenones such as dimethoxyacetophenones (sold under the Trade name "Irgacure 651"); dialkylhydroxyacetophenones such as dimethylhydroxyacetophenone (sold under the Trade name "Darocure 1173"); substituted dialkylhydroxyacetophenone alkyl ethers such compounds of formula

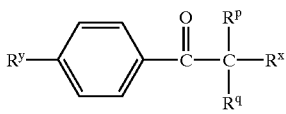

where $R^y$ is alkyl and in particular 2,2-dimethylethyl, $R^x$ is hydroxy or halogen such as chloro, and $R^p$ and $R^q$ are independently selected from alkyl or halogen such as chloro (examples of which are sold under the Trade names "Darocure 1116" and "Trigonal P1"); 1-benzoylcyclohexanol-2 (sold under the Trade name "Irgacure 184"); benzoin or derivatives such as benzoin acetate, benzoin alkyl ethers in particular benzoin butyl ether, dialkoxybenzoins such as dimethoxybenzoin or deoxybenzoin; dibenzyl ketone; acyloxime esters such as methyl or ethyl esters of acyloxime (sold under the trade name "Quantaqure PDO"); acylphosphine oxides, acylphosphonates such as dialkylacylphosphonate, ketosulphides for example of formula

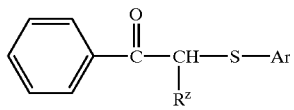

where $R^z$ is alkyl and Ar is an aryl group; dibenzoyl disulphides such as 4,4'-dialkylbenzoyldisulphide; diphenyldithiocarbonate; benzophenone; 4,4'-bis(N,N-dialkylamino)benzophenone; fluorenone; thioxanthone; benzil; or a compound of formula

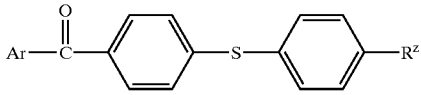

where Ar is an aryl group such as phenyl and $R^z$ is alkyl such as methyl (sold under the trade name "Speedcure BMDS").

Such compositions may be used in applications where it is possible to deliver uv radiation, for example by means of a fibre optic conductor, so as to cause the adhesive or sealant to cure.

Other conventional polymerization initiators including free radical initiators, as are known in the art can be employed.

In another embodiment, the compound of formula (I) is one which will polymerise following initiation by exposure to an electron beam as is understood in the art.

Thermally curable adhesive or sealant compounds of formula (I) can be produced and used in circumstances where heating to the desired temperature is possible, for example in the production of laminates.

The nature of the electron withdrawing group or groups in the compound of formula (I) will depend upon its position in relation to the double bond it is required to activate, as well as the nature of any other functional groups within the compound.

Initiators, where required, will be present in an amount which is sufficient to induce the required reaction in an appropriate time period. Typically, the composition will comprise from 1–10% w/w initiator, suitably about 4–6% w/w initiator depending upon the nature of the compound of formula (I), the type of initiator used, the intended function etc.

In a particular embodiment, the dotted bonds shown in Formula (I) are absent. Thus, certain compounds of formula (I) can be represented as formula (IA)

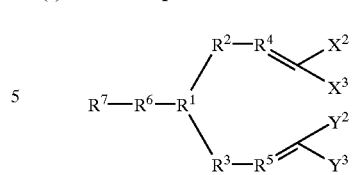

(IA)

where $R^1$, $R^2$, $R^3$, $R^4$, $R^5$, $R^6$, $R^7$, $X^2$, $X^3$, $Y^2$ and $Y^3$ are as defined above in relation to formula (I).

In a preferred embodiment, $R^1$ and $R^6$ form an electron withdrawing group. In this case, it is preferred that $R^2$ and $R^3$ are groups $(CR^8R^8)_n$ and $R^4$ and $R^5$ are CH groups.

For example, $R^1$ is a heteroatom or a substituted heteroatom which has electron withdrawing properties, for example a group $N^+R^{12}$ $(Z^{m-})_{1/m}$, $S(O)_pR^{13}$, B, $P(O)_qR^{14}$ or $Si(R^{15})$ where $R^{12}$, $R^{13}$, $R^{14}$ and $R^{15}$ are independently selected from hydrogen or hydrocarbyl, Z is a anion of valency m, p is 0, 1 or 2, and q is 0, 1, 2 or 3; and $R^6$ is a bond.

Suitably hydrocarbyl groups for $R^{12}$, $R^{13}$, $R^{14}$ and $R^{15}$ include alkyl and alkenyl groups.

The nature of the anion Z, where present, will affect the properties of the final adhesive or sealant and in particular, its conductivity. Suitable anions for the Z group include halide ions such as fluoride, chloride, bromide or iodide, borides such as boron tetrafluoride; carboxylic acid esters such as those of formula $R^{14}C(O)O^-$ where $R^{14}$ is an optionally substituted hydrocarbyl group group such as haloalkyl, in particular trifluoromethyl; and other anionic groups such as mesylate and tosylate. In general, the water permeability of the ultimate polymer will vary as follows:

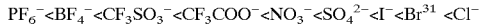

Other factors which affect water permeability of the adhesive or sealant is the nature of any group to which the group of sub-formula (I) is attached. When this contains for example perhaloalkyl substituents such as perfluoroalkyl, it will be largely water impermeable as compared to adhesives or sealants which have alkylene bridging groups optionally interposed with say oxygen.

High water permeability provides the advantage that any excess adhesive or sealant applied can be easily removed using water.

Alternatively, $R^1$ is a group CH and $R^6$ is a group —C(O)O— or —OC(O)— or —S(O)$_2$—. Suitably $R^6$ is a group —C(O)O— or —OC(O)—.

Most preferably, the combination of $R^1$ and $R^6$ forms an amide group, where $R^1$ is a nitrogen atom and $R^6$ is a carbonyl group. Alternatively the combination forms a sulphonamide group where $R^1$ is a nitrogen atom and $R^6$ is a sulphonyl group. The nitrogen atom of the amide group may or may not form part of a group $N^+R^{12}(Z^{m-})_{1/m}$ as described above, depending upon the nature of the compound of formula (I) and the nature of any initiator used in the composition. In other words, the nitrogen may be quaternised or may not since the electron withdrawing effect of the group $R^6$ in this case will produce the necessary level of activation of the double bond.

Alternatively, where the activation is effected by electron withdrawing groups at a position indicated by $R^2$ or $R^3$, suitable electron withdrawing groups $R^9$ and $R^{10}$ include carbonyl, nitrile, trifluoromethyl, acyl or nitro, preferably $R^9$ and $R^{10}$ together form an oxo group.

Where $R^{11}$ is an electron withdrawing group, it is suitably acyl, nitrile or nitro.

Preferably $X^2$, $X^3$, $Y^2$ and $Y^3$ are all hydrogen or all fluorine and in particular they are all hydrogen.

A preferred group of the compounds for use in the method of the invention is a compound of structure (II)

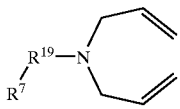

(II)

where $R^7$ is as defined in relation to formula (I) and $—R^{19}—$ is C(O), C(S) or S(O)$_2$. Preferably $R^{19}$ is a group $—C(O)—$.

A furthers preferred group of compounds for use in the method of the invention are compounds of compounds of formula (IIA)

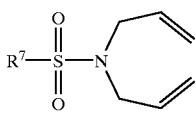

(IIA)

where $R^7$ is as defined in relation to formula (I).

Preferably $R^7$ is an optionally substituted hydrocarbyl group, a perhaloalkyl group or an amide.

Suitable optional substituents for hydrocarbyl groups $R^7$ in the compound of formula (I) include functional groups as defined above, such as cyano. Preferably, $R^7$ includes an unsaturated moiety, in particular any aryl or alkenyl group, or a substituent which involves a double bond such as is found in a carbonyl group.

In particular $R^7$ is an optionally substituted alkyl, alkenyl, alkynyl or aryl group.

Preferred substituents for $R^7$ include carboxy or salts or esters thereof and acyloxy. Suitable salts for carboxy groups are metal salts, in particular alkali metal salts such as lithium, sodium or potassium, alkaline earth metal salts such as magnesium or calcium salts or organic salts such as quaternary ammonium salts. Suitable quaternary ammonium salts contain optionally substituted hydrocarbyl groups. In particular, they comprise alkyl groups substituted by hydroxy or interposed with oxygen atoms. Multiple salts containing more than one molecule of formula (I) may be formed where the cation has a valency of greater than one. In particular, hydrocarbyl group having more than one quaternary ammonium substituent will have the effect of associating molecules of formula (I) together as illustrated hereinafter.

Suitable ester groups include optionally substituted hydrocarbyl esters such as optionally substituted alkyl, of aryl esters, where the optional substituents include for example functional groups such as halo.

Where $R^7$ is a perhaloalkyl group, it is suitably comprises from 1 to 3 carbon atoms, such as perfluoromethyl.

Suitable amide groups $R^7$ are hydrocarbyl amides or hydrocarbyl sulphonamides, and in particular include dialkenyl substituted amides such as those of sub formula (III)

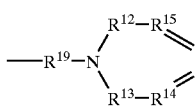

(III)

where $R^{19}$ is as defined above in relation to formula (II) $R^{12}$ and $R^{13}$ are selected from groups defined above for $R^2$ and $R^3$ in relation to formula (I) and $R^{14}$ and $R^{15}$ are selected from groups defined above as $R^3$ and $R^4$ in relation to formula (I). In particular, $R^{12}$ and $R^{13}$ are $—CH_2—$ or $—CH_2CH_2—$ groups and $R^{14}$ and $R^{15}$ are $—CH—$ groups. The amide groups may themselves become involved in the polymerization process, thus allowing branched or network polymers to be formed as the adhesive or sealant is cured.

Suitably $R^{19}$ is a group C(O).

Particular examples of compounds of formula (II) are listed in Table 1

TABLE 1

| Compound No. | $R^7$ | $R^{19}$ |
|---|---|---|
| 1 | $CH_3$ | C(O) |
| 2 | $CF_3$ | C(O) |
| 3 | $C_6H_5$ | C(O) |
| 4 | $CHCH_2$ | C(O) |
| 5 | $CH_2OCOCHCH_2$ | C(O) |
| 6 | $CH_2CH_2COOH$ | C(O) |
| 7 | $C(O)N(CH_2CH=CH_2)_2$ | C(O) |
| 8 | $CH_2C(O)N(CH_2CH=CH_2)_2$ | C(O) |
| 9 | $CH_2CH_3$ | C(O) |
| 10 | $CH_2OCOCH_2CH_3$ | C(O) |
| 11 | $CH_2CH_2CH_2COOH$ | C(O) |
| 12 | $(CH_2)_5CH_3$ | C(O) |
| 13 | $CH_3$ | $S(O)_2$ |
| 14 | $CF_3$ | $S(O)_2$ |
| 15 | $C_6H_5$ | $S(O)_2$ |
| 16 | $CHCH_2$ | $S(O)_2$ |
| 17 | $CH_2OCOCHCH_2$ | $S(O)_2$ |
| 18 | $CH_2CH_2COOH$ | $S(O)_2$ |
| 19 | $S(O)_2N(CH_2CH=CH_2)_2$ | $S(O)_2$ |
| 20 | $CH_2S(O)_2N(CH_2CH=CH_2)_2$ | $S(O)_2$ |
| 21 | $CH_2CH_3$ | $S(O)_2$ |
| 22 | $CH_2OCOCH_2CH_3$ | $S(O)_2$ |
| 23 | $CH_2CH_2CH_2COOH$ | $S(O)_2$ |
| 24 | $(CH_2)_5CH_3$ | $S(O)_2$ |
| 25 | $CH_2CN$ | C(O) |
| 26 | $CH_2CN$ | $S(O)_2$ |
| 27 | $C(=CH_2)CN$ | C(O) |
| 28 | $CH_2CH_2C(O)N(CH_2CH_2OH)_2$ | C(O) |
| 29 | $CH_2C(O)N(CH_2CH_2OH)_2$ | C(O) |
| 30 | $CH_2Br$ | C(O) |
| 31 | $CH_2OH$ | C(O) |
| 32 | $(CF_2)_3COOH$ | C(O) |
| 33 | $CH_2CH_2COO^-Li^+$ | C(O) |
| 34 | $CH_2CH_2CH_2COO$—(3-fluorophenyl) | C(O) |
| 35 | $C(=CH_2)CH_2COOH$ | C(O) |
| 36 | $CH_2C(=CH_2)COOH$ | C(O) |
| 37 | $CH=CHCOOH$ | C(O) |
| 38 | —(phenyl)—OH | C(O) |
| 39 | $CH=CHCOOH$ | C(O) |
| 40 | $C(CH_3)=CHCOOH$ | C(O) |
| 41 | $CH=$(phenyl)$COOH$ | C(O) |

TABLE 1-continued

| Compound No. | $R^7$ | $R^{19}$ |
|---|---|---|
| 42 | $(CH_2)_3OH$ | $C(O)$ |
| 43 | $(CH_2)_3OC(O)CH=CH_2$ | $C(O)$ |
| 44 | $OCH_2$—⟨phenyl⟩ | $C(O)$ |
| 45 | $(CH_2)_3C(O)NH(CH_2)_3Si(OCH_3)_3$ | |
| 46 | $CH_2CH_2COO^-N^+H(CH_2CH_2OH)_3$ | $C(O)$ |
| 47 | $CH_2CH_2COO^-N^+H_3C(CH_2OH)_3$ | $C(O)$ |
| 48+ | $CH_2CH_2COO^-N^+H_3(CH_2)_3[O(CH_2)_2]_2O(CH_2)_3NH_3^+$ | |

+In this compound the second quaternary ammonium ion acts as a counter-ion for an acid compound of formula (I).

A further sub-group of the compounds of formula (I) are compounds of formula (IV)

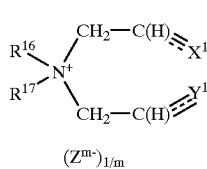

[IV]

where $X^1$, $Y^1$, Z, m and the dotted lines are as defined above, the hydrogen atoms in bracket are absent when the dotted lines represent the presence of a bond, $R^{16}$ and $R^{17}$ are independently selected from hydrogen and hydrocarbyl which may be optionally substituted by hydroxy, in particular alkyl and alkenyl such as prop-2-enyl or a hydroxyalkyl such as hydroxyethyl or a group of formula —$C((CH_2)_dOH)_a(H)_b$ where a is an integer of from 1 to 3 and b is 0 or an integer of 1 or 2 provided that a+b is 3, and d is an integer of from 1 to 6, preferably 2 or 3.

The presence of hydroxy groups as substitutents $R^{16}$ and $R^{17}$ groups may be preferred in that these groups can make the compounds of formula (IV) water soluble, allowing for the possibility that water based adhesives or sealants can be produced.

Particular examples of compounds of formula IV include compounds of formula (IVA)

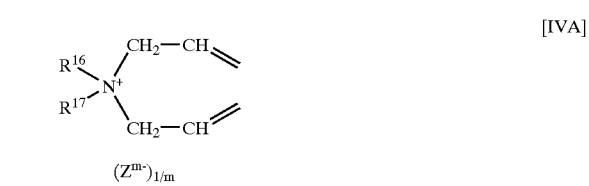

[IVA]

where $R^{16}$, $R^{17}$ Z and m are as defined in relation to formula (IV) and some are listed in Table 2.

TABLE 2

| Compound No | $R^{16}$ | $R^{17}$ | Z |
|---|---|---|---|
| 49 | H | $CH_2CH=CH_2$ | $Cl^-$ |
| 50 | $CH_2CH=CH_2$ | $CH_2CH=CH_2$ | $Br^-$ |
| 51 | $CH_2CH=CH_2$ | $C(CH_2CH_2OH)_3$ | $Cl^-$ |
| 52 | $CH_2CH=CH_2$ | $C(CH_2CH_2CH_2OH)_3$ | $Cl^-$ |
| 53 | H | $(CH_2)_7CH_3$ | $Cl^-$ |
| 54 | H | $(CH_2)_6OH$ | $Cl^-$ |
| 55 | H | $(CH_2)_6OC(O)CH=CH_2$ | $Cl^-$ |
| 56 | H | $(CH_2)_2N^+H(CH_2CH=CH_2)_2$ | $Cl^-$ |
| 57 | H | $(CH_2)_2N^+H(CH_2CH=CH_2)_2$ | $PF_6^-$ |
| 58 | $CH_2CH_2CH_2OH$ | $CH_2CH_2CH_2OH$ | $Br^-$ |
| 59 | H | $CH_2CH=CH_2$ | $PF_6^-$ |
| 60 | $CH_2CH=CH$ | —$(CH_2)_4$—$N^+$—$(CH_2)_3$—$N^+$ (with allyl groups, $Br^-$, $Br^-$) | |

Other compounds of formula (I) include those listed in Table 3.

TABLE 3

| No. | $R^1$ | $R^2$ | $R^3$ | $R^4$ | $R^5$ | $R^6$ | $R^7$ | $X^{1*}$ | $Y^{1*}$ |
|---|---|---|---|---|---|---|---|---|---|
| 61 | N | $C(O)$ | $CH_2$ | CH | CH | bond | H | $CH_2$ | $CH_2$ |
| 62 | N | $CH_2$ | $CH_2$ | C | C | $C(O)$ | $(CH_2)_3COOH$ | CH | CH |
| 63 | CH | bond | bond | CH | CH | $OC(O)$ | $CH=CH_2$ | $CH_2$ | $CH_2$ |

*where $X^1$ and/or $Y^1$ are divalent moieties, the relevant dotted bonds in formula (I) are absent.

Certain compounds of formula (I) are novel and these form a further aspect of the invention.

In particular, there is provided a compound of formula

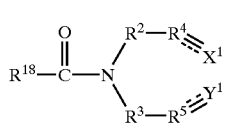

[V]

where $R^2$, $R^3$, $R^4$, $R^5$, $X^1$ and $Y^1$ and the dotted lines are as defined in relation to formula (I) and $R^{18}$ is $R^7$ as defined in relation to formula (I) provided that where $R^2$ and $R^3$ are both $CH_2$ and $R^4$ and $R^5$ are both CH, $R^{18}$ is other than methyl, chloromethyl or trichloromethyl.

Preferably, $R^{18}$ is other than alkyl or haloalkyl including perhaloalkyl.

In particular, the compound of formula (V) is a compound of formula (VA)

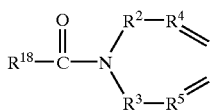

[VA]

where $R^2$, $R^3$, $R^4$, $R^5$ and $R^{12}$ is as defined in relation to formula (V).

Novel compounds of formula (IV) above include those where $R^{16}$ and/or $R^{17}$ are alkenyl or alkynyl groups and these form a further aspect of the invention.

Adhesive or sealant compositions of the invention may include additional reagents such as solvents, plasticisers, curing agents, dyes, fillers etc as is understood in the art. Preferably, as discussed above, the compositions include water as a solvent. However, where the compound of formula (I) has a relatively high viscosity, an organic solvent such as dichloromethane, acetone, tetrahydrofuran etc. may be present in order to ensure that the composition is homogenous and will spread well. Suitably, any solvent will be present in an amount of from 200 to 300% w/w.

Compounds of formula (I) may be prepared by conventional methods. For example, they may be prepared by reacting a compound of formula (VI)

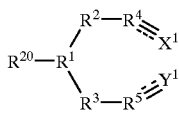

[VI]

where $R^1$, $R^2$, $R^3{}_1$, $R^4$, $R^5$, $X^1$, $Y^1$ and the dotted lines are as defined in relation to formula (I), and $R^{20}$ is hydrogen or hydroxy, with a compound of formula (VII)

$$R^7\text{—}R^6\text{—}Z^1 \qquad \text{(VII)}$$

where $R^6$ and $R^7$ are as defined in relation to formula (I) and $Z^1$ is a leaving group.

Suitable leaving groups $Z^1$ include halogen in particular bromo, mesylate or tosylate. The reaction is suitably effected in an organic solvent such as tetrahydrofuran, dichloromethane, toluene, alcohols such as ethanol, methanol, or ketones such as butanone and elevated temperatures in the region of the boiling point of the solvent.

Preferably the reaction is effected in the presence of a base such as potassium carbonate.

Compounds of formulae (VI) and (VII) are either known compounds or they can be prepared from known compounds by conventional methods.

Adhesives in accordance with the invention can be used in a variety of applications depending upon the precise nature of the compounds of formula (I). For example, they may be used to form bonds between glass surfaces, surfaces between metals and glass and in the production of laminates and shatter-proof glass. By forming the compound of formula (I) so that it includes a charged group, the adhesives may provide an electrically conducting layer.

Adhesives of the invention may also have applications in biomedical fields. For example, biocompatible compounds of formula (I) may be used to adhere molds or splints in place, or to adhere tissues, or in the formation of internal welds. Biocompatible compounds preferably include amide groups as the electron withdrawing groups as these most closely resemble naturally occurring amino acids.

Thus the invention further provides a method of adhering surfaces to one another, said method comprising applying to at least one surface, a compound of formula (I) as described above, contacting said treated surface with the surface to which it is to be adhered, and allowing the compound of formula (I) to polymerise.

The invention will now be particularly described by way of example with reference to the accompanying drawing which illustrates the polymerization of a compound of formula (I).

EXAMPLE 1

Preparation of Compound No 28 in Table 2

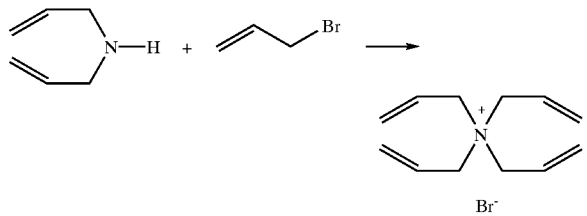

Diallylamine (10.0 g, 0.103 mol), allyl bromide (25.41 g, 0.21 mol) and potassium carbonate (20 g) were refluxed in ethanol. Solids were removed by filtration and the solvents were removed in vacuo to leave a yellow oil.

EXAMPLE 2

Preparation of Compound No 53 in Table 2

Step 1

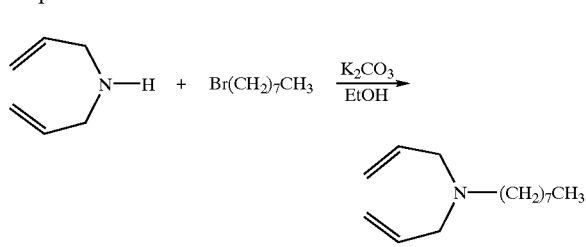

1-Bromooctane (15.0 g, 0.078 mol), diallylamine (8.26 g, 0.085 mol) and potassium carbonate (11.75 g, 0.085 mol) were refluxed in ethanol (1000 cm$^3$) for 18 hours. Solids were removed by filtration and the solvents were removed in vacuo to leave a yellow oil. Column chromatography (silica gel/dichloromethane) followed by removal of solvent in vacuo and thorough drying gave 12.9 g, 79% of light yellow oil.

$^1$HNMR (CDCl$_3$) δ: 0.85(t, 3H), 1.80(s, br, 10H), 1.45(s, br, 2H), 2.40(5, 2H), 3.15(d, 4H), 5.10(m, 4H), 5.85(m, 2H).

Ir vmax (thin film): 3082, 2932, 2860, 2806, 2355(w), 1751(w), 1709(w), 1644(m), 1463, 1419, 1379, 1262, 1083, 996, 919, 613 cm$^{-1}$ Step 2

Quaternisation was effected by reaction with methanolic hydrochloric acid (6N). Other salts could be produced by reaction with the appropriate acid.

EXAMPLE 3

Preparation of Compound No. 3 in Table 1

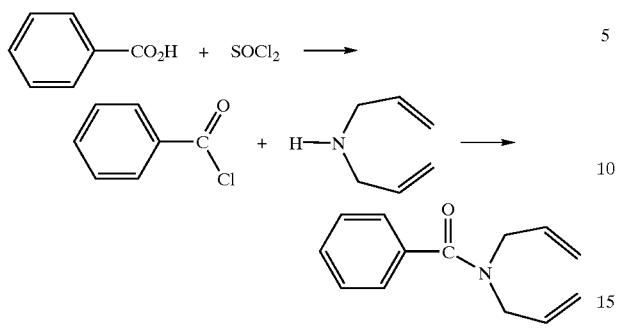

Benzoic acid (20.0 g, 0.164 mol) was placed in thionyl chloride (23.80 g, 0.20 mol) and the mixture heated to approximately 80° C. with stirring for 3 hours. Excess thionyl chloride was removed in vacuo and the residue cooled to approximately −5° C. in a salt/ice bath. Diallylamine (19.50 g, 0.20 mol) in dry dichlotomethane (20 cm$^3$) was added dropwise with much evolution of HCl gas. After complete addition, the resultant brown solution was allowed to rise to room temperature and left stirring for one hour. It was then washed with 3N HCl (150 cm$^3$), saturated $K_2CO_3$ solution (150 cm$^3$) and brine (150 cm$^3$), then finally dried over $MgSO_4$. Removal of solvent gave a brown oil which was passed through a silica gel column using ethyl acetate as the eluent. Removal of solvent in vacuo gave a yellow oil. 27.10 g, 82%.

$^1$HNMR (CDCl$_3$) δ: 3.90(s, br, 2H), 4.10(s, br, 2H), 5.20(m, 4H), 5.70(s, br, 1H), 5.85(s, br, 1H), 7.40(m, 5H)

Ir vmax (thin film) 3087, 1640, 1498, 1456, 1413, 1262, 1120, 991, 928, 788, 703 cm$^{-1}$

EXAMPLE 4

Preparation of Compound No 12 in Table 1

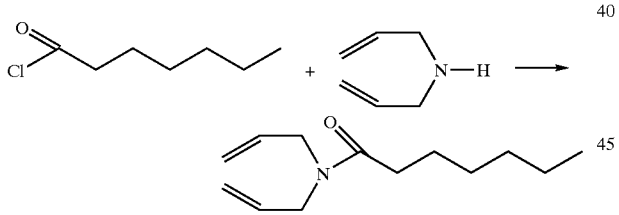

Heptanoyl chloride (25.0 g, 0.168 mol) was placed in dry dichloromethane (100 cm$^3$) and the solution cooled to −5° C. in a salt-ice bath. Diallylamine (17.5 g, 0.18 mol) in dry dichloromethane (25 cm$^3$) was added dropwise with much evolution of HCl gas. The resultant solution was allowed to rise to room temperature then poured into 3N HCl (300 cm$^3$) and stirred vigorously for ten minutes. The organic layer was removed by separation and to the aqueous layer was added ammonium chloride. This was then re-extracted with dichloromethane (2×100 cm$^3$) and the three organic extracts combined and dried over $MgSO_4$. Removal of solvent in vacuo left a brown oil (one spot on tlc-silica gel/ethyl acetate) which was passed through a silica gel column using ethyl acetate as the eluent. Removal of solvent in vacuo gave a yellow oil. 32.0 g, 91%.

$^1$HNMR (CDCl$_3$) δ: 0.90(t, 3H), 1.35(m, 6H), 1.65(quin, 2H), 2.35(t, 2H), 3.90(m, 2H), 4.0(m, 2H), 5.15(m, 4H), 5.75(m, 2H).

Ir vmax (thin film): 2933, 2861, 2338, 1722, 1655, 1563, 1466, 1415, 1227, 1114, 995, 923 cm$^{-1}$

EXAMPLE 5

Preparation of Compound No.7 in Table 1

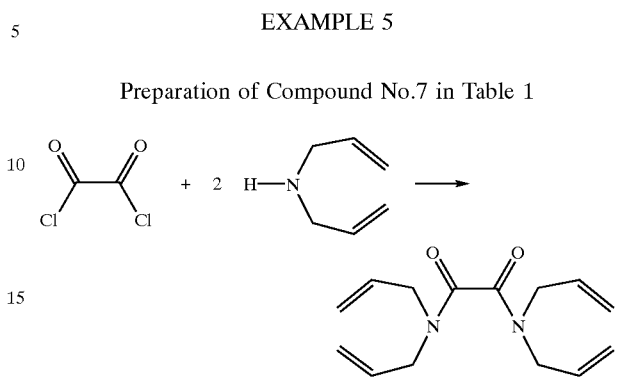

Oxyalyl Chloride (25.0 g, 0,197 mol) was placed in dry dichloromethane (150 cm$^3$) and cooled to −5° C. and stirred. The diallylamine (48.6 g, 0.50 mol) in dry dichloromethane (50 cm$^3$) was slowly added dropwise (much HCl evolved) keeping temperature below 20° C. After addition the solution was stirred at room temperature for thirty minutes and then washed with 3N HCl (100 cm$^3$), saturated $K_2CO_3$ (100 cm$^3$), brine (100 cm$^3$), and finally dried over $MgSO_4$. Removal of solvent left a brown oil (one spot by tic, silica gel/EtOAc). The oil was passed through a silica gel column using ethyl acetate as the eluent. Removal of solvent left a yellow oil. 42.50 g, 87%.

$^1$HNMR (CDCl$_3$) δ: 3.85(m, 4H), 4.0(m, 4H), 5.15(m, 8H), 5.80(m, 4H)

Ir vmax (thin film): 3088, 2991, 1654, 1488, 1413, 1285, 1215, 1128, 996, 930, 783, 720 cm−1

EXAMPLE 6

Preparation of Compound No. 4 in Table 1

$H_2C=CHC(O)Cl + HN(CH_2CH=CH_2)_2 \rightarrow$
$H_2C=CHC(O)N(CH_2CH=CH_2)_2$

Acryloyl chloride (25.0 g, 0.28 mol) was placed in dry dichloromethane (150 cm$^3$) and cooled to −5° C. in a salt/ice bath and stirred. Diallylamine (29.15 g, 0.30 mol) in dry dichloromethane (50 cm$^3$) was added dropwise over ~1 h* and the resultant solution allowed to rise to room temperature and stirred for 30 minutes. The solution was treated with 3N HCl (100 cm$^3$) saturated $K_2CO_3$ solution (100 cm$_3$) and brine (100 cm$^3$) then dried over $MgSO_4$. Removal of solvent gave a brown oil. The oil was passed through a silica gel column using ethyl acetate as eluent. Removal of solvent gave the desired product as a yellow oil 37.1 g 89%.

* evolution of HCl

Ir vmax (thin film): 2988, (1726), 1657, 1618, 1470, 1443, 1226, 1196, 1077, 989, 926, 795 cm$^{-1}$ $^1$HNMR (CDCl$_3$) δ: 3.95 (d, 2H), 4.05 (d, 2H), 5.15 (m, 4H), 5.65 (m, 1H), 5.75 (m, 2H), 6.90 (m, 2H)

EXAMPLE 7

Preparation of Compound 8 in Table 1

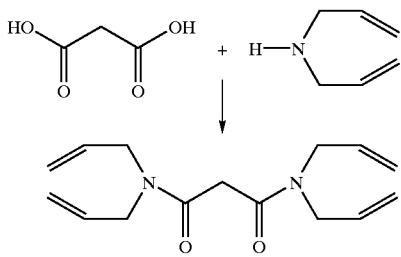

Malonic acid (16.23 g, 0.156 mol), diallylamine (31.1 g, 0.320 mol) and 1,3-dicyclohexylcarbodiimide (66.0 g, 0.320 mol) were placed in dry dichloromethane and the mixture stirred for 18 hours at room temperature. The copious quantity of 1,3-dicyclohexyl-urea was removed by filtration (Whatman No. 1 filter paper) and the organic filtrate washed with 3N HCl (150 cm$^3$), then saturated potassium carbonate followed by water (150 cm$^3$). The solution was dried over MgSO$_4$ and removal of solvent gave a brown oil. The oil was passed through a silica gel column using ethyl acetate as eluent. Further decoloration was achieved using charcoal and dichloromethane/40/60 petrol (1:1) as solvent. Filtration and removal of solvent in vacuo gave a yellow/brown oil. 33.70 g, 87%.

$^1$HNMR (CDCl$_3$) δ: 3.55(s, 2H), 4.04(d, 8H), 5.15(m, 8H), 5.80(m, 4H).

Ir vmax (thin film): 2987, 2934, 1652, 1414, 1310, 1223, 1193, 1136, 996, 922, 852, 700, 556 cm$^{-1}$.

EXAMPLE 8

Preparation of Compound No. 6 in Table 1

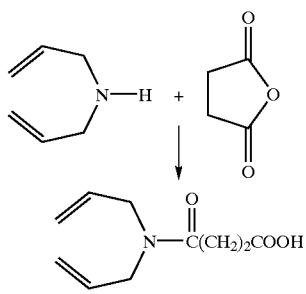

Succinic anhydride (50.0 g, 0.5 mol) was placed in a dry dichloromethane (400 cm$^3$) and stirred and cooled to −5° C. in a salt/ice bath. Diallylamine (48.6 g, 0.5 mol) in dry Dichloromethane (100 cm$^3$) was added dropwise over 1 hour keeping the temperature at >20° C. As addition proceeded, the succinic anhydride, suspended in dichloromethane became less evident until all had reacted to form a pale yellow solution. The solution was washed in 3N HCl solution (200 cm$^3$), saturated K$_2$CO$_2$ (200 cm$^3$) then water (200 cm$^3$) and finally dried over MgSO$_4$. Removal of solvent left a light yellow oil (of one spot purity on t.l.c.). 95.46 g, 96%.

$^1$HNMR (CDCl$_3$) δ: 2.65(m, 4H), 3.95(d, 2H), 4.0.5(d, 2H), 5.15(m, 4H), 5.75(m, 2H)

Ir vmax (thin film): 3088(br), 1737, 1650, 1480, 1418, 1233, 1176, 995, 928,. 829, 558 cm$^{-1}$

EXAMPLE 9

Preparation of compound No 2 in Table 1

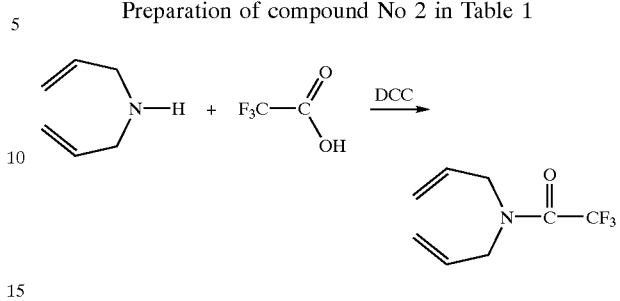

Diallylamnine (17.0 g, 0.185 mol) and 1,3-dicyclohexylcarbodiimide (36.12 g, 0.175 mol) were dissolved in dry dichioromethane (150 cm$^3$) and the solution cooled to 0° C. Trifluoroacetic acid (20.0 g, 0.175 mol) in dry dichioromethane (50cm$^3$) was added dropwise over 1 hour and the whole was left stirring at room temperature for 72 hours. The 1,3-dicyclohexylurea was removed by filtration and the solvent removed in vacuo to leave a yellow oil. Column chromatography (silica gel-dichloromethane) followed by removal of solvent in vacuo gave a pale yellow oil which crystallised slowly on standing. 26.67 g, 79.0%.

$^1$HNMR (CDCl$_3$) δ: 4.0(d, 4H), 5.20 (m, 4H),. 5.75(m, 2H)

Ir vmax (thin film) : 2935, 2866, 1698, 1559, 1454, 1348, 1305, 1160, 1050, 994, 926, 895 cm$^{-1}$

EXAMPLE 10

Preparation of Compound No 25 in Table 1

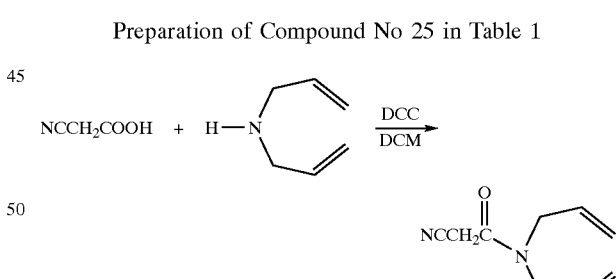

Cyanoacetic acid (25.0 g, 0.294 mol) in dry dichloromethane (100 cm$^3$) was added dropwise to a solution of diallylamine (29.0 g, 0.30 mol) and 1,3-dicyclohexylcarbodiimide (64.0 g, 0.31 mol) in dry dichloromethane (250cm$^3$). The mixture was left stirring for 15 hours at room temperature. The 1,3-dicyclohexylurea was removed by filtration and the solvent removed to leave a brown oil. Column chromatography (silica gel-dichloromethane) followed by removal of solvent in vacuo left a light yellow oil. 40.50 g, 84%.

¹HNMR (CDCl₃) δ: 3.75(s, 2H), 4.0(d, 2H), 4.10(d, 2H), 5.40(m, 4H), 5.90(m, 2H).

Ir νmax (thin+film): 3091, 2931, 2261, 1674, 1448, 1316, 1229, 1192, 1139, 996, 931, 820cm⁻¹.

EXAMPLE 11

Preparation of Compound no 61 in Table 3

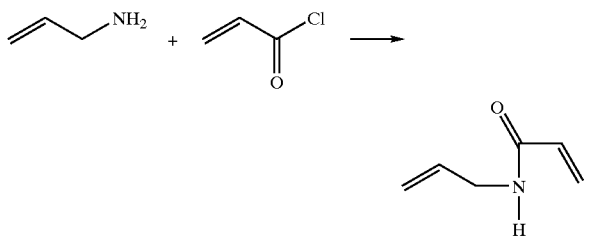

Acryloyl chloride (16.5 g, 0.180 mol) was dissolved in dry dichloromethane (50 cm³) and the solution was cooled to −5° C. in a salt/ice bath and stirred. The allylamine (5.0 g, 0.087 mol) in dry dichloromethane (25 cm³) was added dropwise over 30 minutes and the resultant solution was allowed to rise to room temperature and stirred for a further 30 minutes. The solution was treated with 3M HCl (50 cm³), saturated K₂CO₃ solution (50 cm³) and brine (50 cm³) then dried over MgSO₄. Removal of solvent gave a yellow oil. The oil was passed through a silica gel column using ethyl acetate as the eluent. Removal of solvent gave a yellow oil. 8.90 g, 92%.

¹HNMR (CDCl₃) δ: 3.95(t, 2h), 5.15(m, 2h), 5.60(m, 1h), 5.85(m, 1h), 6.20(m, 2h), 6.70(s, br, 1H)

Ir νmax (thin film) 3289, 3084, 1664, 1628, 1549, 1412, 1246, 1070, 989, 922, 808 cm⁻¹

EXAMPLE 12

Preparation of Compound 13 in Table 1

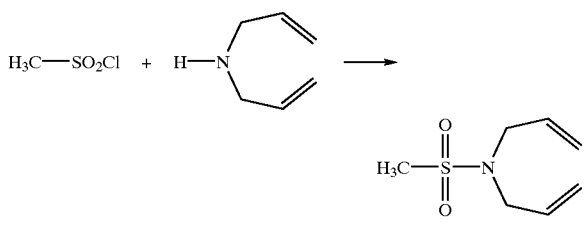

Methane sulphonyl chloride (10.0 g, 0.087 mol), diallyamine (8.75 g, 0.090 mol) and potassium carbonate (10 g) were placed in sieve-dried butanone (100cm³) and the mixture was refluxed with stirring for 3 hours. Thin layer chromatography (ethyl acetate) showed a product spot at ~Rf 0.5 with no evidence of diallyamine remaining. The reaction mixture was filtered (Whatman No. 1 filter paper) and the solvent was removed in vacuo to leave a brown oil. The oil was purified using column chromatography using silica gel and ethyl acetate-petrol 40/60 (1:1) as eluent. Removal of solvent in vacuo gave the product as a yellow oil (12.30 g, 80%)

Ir νmax (thin film): 3089, 2990, 1331(s), 1150, 1046, 996, 934, 793, 733cm⁻¹.

¹HNMR (CDCl₃) δ: 2.90(s,3H), 3.85(d, 4H)m 5.2(m,4H), 5.80(m,2H).

Other sulphonamides in Table 1 can be prepared by an analogous method.

EXAMPLE 13

Preparation of Adhesive Compositions

5% w/w Irgacure 184 was added to a compound 4 in Table 1. The mixture was warmed to achieve complete homogeneity.

The mixture was then applied to the surface of a glass plate so as to form a thin layer thereon. A second glass plate was then placed over the adhesive and the two plates squeezed together. Exposure of this structure to a Philips UVA (75W) sunlamp for approximately 30 seconds resulted in permanent bonding between the two glass surfaces.

Similar results were achieved with other low viscosity monomers described herein.

For more viscous monomers such as Compound 11 in Table 1, an organic solvent, in particular dichloromethane, (%W/W) was added to assist in the formation of a homogenous preparation.

EXAMPLE 14

Preparation of Compound No. 11 in Table 1

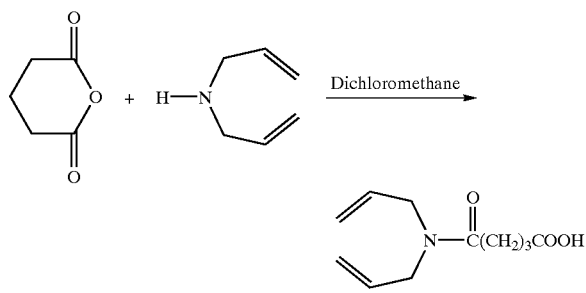

Glutaric anhydride (30.0 g, 0.26 mol) was placed in dry dichloromethane (150 cm³) and the mixture cooled (salt/ice bath) and stirred. Diallylamine (27.20 g, 0.28 mol) in dry dichloromethane (50 cm³) was added dropwise to form a clear yellow solution which was stirred for a further 30 min. It was then washed with 3N HCl (200 cm3) then brine (200 cm3) and dried over MgSO4. Removal of solvent left a yellow oil, 53.7 g, 98%.

Ir νmax (thin film): 2500–3600, 1715, 1605, 1640, 1480, 1410, 1215, 995, 920 cm⁻¹.

¹HNMR (CDCl₃) δ: 1.95 (quin, 2H), 2.45(m, 4H), 3.90(d, 2H), 3.98(d, 2H), 5.15(m, 4H), 5.75(m, 2H), 11.10(s, 1H).

EXAMPLE 15

Preparation of Compound No. 29 in Table 1

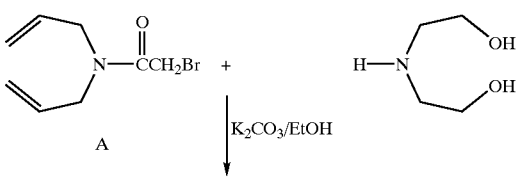

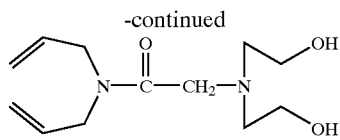

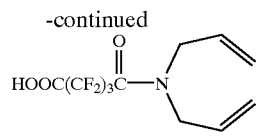

Amide A (5.0 g, 0.023 mol), diethanolamine (2.40 g, 0.023 mol) and potassium carbonate (3.45 g (0.025 mol) in ethanol (50 cm3) were stirred together at reflux for 15 h. The solids were removed by filtration (Whatman No. 1) and the solvent removed in vacuo to leave a brown oil. Column chromatography (silica gel/ethyl acetate) followed by removal of solvent in vacuo and thorough drying left 4.8 g, 87% as a yellow oil.

Ir vvmax (thin film): 3650–3100, 2937, 1646(S), 1419, 1354, 1229, 1131, 995, 927, 754 cm$^{-1}$.

$^1$HNMR (CDCl$_3$) δ: 2.80(t, 2H), 3.40(t, 2H), 3.50(s, 2H), 3.90(d, 2H), 4.0(d, 2H), 5.15(m, 4H), 5.85(m, 2H).

EXAMPLE 16

Preparation of Compound No. 30 in Table 1

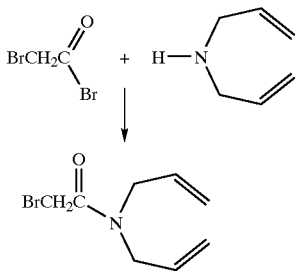

Bromoacetyl bromide (30.0 g, 0.15 mol) was dissolved in dry dichloromethane (260 cm$^3$) and the solution stirred at room temperature. Diallylamine (14.50 g, 0.15 mol) in dry dichloromethane (50 cm$^3$) was added dropwise with much evolution of HCl gas, after complete addition the solvent was removed in vacuo to give a brown oil. Column chromatography (silica gel/ethyl acetate) followed by removal of solvent gave a yellow oil, 31.4 g, 97%.

Ir vmax (thin film) : 3513, 3087, 2989, 2927, 1657, 1449, 1343, 1257, 1212, 1108, 994, 922, 728, 689, 618, 555 cm$^{-1}$.

$^1$HNMR (CDCl$_3$) δ: 3.85(s, 2H), 3.95(m, 4H), 5.20(m, 4H), 5.80(m, 2H).

EXAMPLE 17

Preparation of Compound No. 32 in Table 1

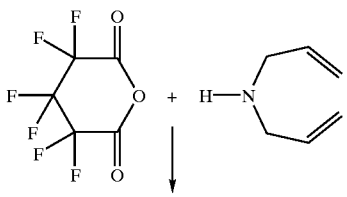

Hexafluoroglutaric anhydride (5.0 g, 0.0225 mol) was dissolved in dry dichloromethane (100 cm$^3$) and the solution was cooled to ~−5° C. in a salt/ice bath. Diallylamine (2.20 g, 0.022 mol) in dry dichloromethane (20 cm$^3$) was added dropwise over 15 minutes and the mixture stirred for 30 minutes at room temperature. Aqueous HCl (6N) (100 cm3) was added and the mixture stirred for 10 minutes. The organic layer was separated and dried over MgSO4. Removal of solvent gave a brown oil, 5.50 g, 77%.

Ir vmax (thin film): 3095, 3650–2500, 1786, 1678(s), 1422, 1244, 1164, 1052, 993 cm−1.

$^1$HNMR (CDCl$_3$) δ: 3.67(~1H, 4.0(d, 2H), 4.05(d, 2H), 5.25(m, 4H), 5.76(m, 2H), 12.0(s, 1H), 5.43(s ~½H), 5.46(d, ~½H)

EXAMPLE 18

Preparation of Compound No. 33 in Table 1

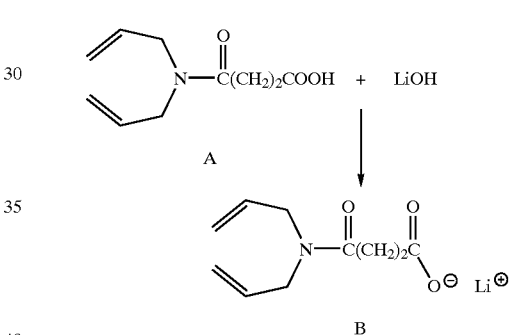

Acid A (5.0 g, 0.027 mol) and lithium hydroxide (648 mg, 0.027 mol) were dissolved in ethanol-water mixture (20 cm$^3$). Solvents were removed in vacuo to leave a white solid which was suspended in acetone. Filtration (No. 1 sinter) followed by washing of the retained solid with acetone (50 cm$^3$) and thorough drying gave the lithium salt B 4.90 g, 96%, as a white powder insoluble in most organic solvents.

Ir vmax (KBr Disc): 3085, 3020, 2980, 2922, 1643(s), 1581(s), 1422, 1347, 1279, 1256, 1213, 1140, 1013, 912, 833, 808, 721, 622, 575 cm$^{-1}$.

EXAMPLE 19

Preparation of Compound No. 34 in Table 1

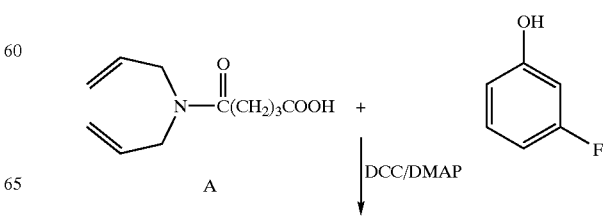

-continued

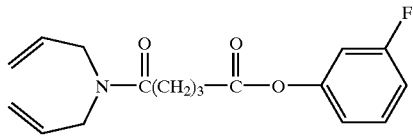

Amidoacid A (10.0 g, 0.047 mol), 3-fluorophenol (5.27 g, 0.047 mol), dicyclohexylcarbodiimide (9.70 g, 0.047 mol) and 4-dimethylaminopyridine (0.50 g ) were stirred together in dry dichloromethane (150 cm$^3$) for 18 h at room temperature. The dicyclohexylurea was removed by filtration (Whatman No. 1 filter paper) and the filtrate washed with 2M KOH solution (100 cm$^3$), then water (100 cm$^3$) and dried over MgSO$_4$. Removal of solvent left a yellow oil which was purified by column chromatography (silica gel) using dichloromethane as the eluent. Removal of solvent left a clear oil, 13.4 g, 93.0%.

$^1$HNMR (CDCl$_3$) δ: 2.09(t, 2H), 2.47(t, 2H), 2.66(t, 2H), 3.88(d, 2H), 3.99(d, 2H), 5.20(m, 4H), 5.78(m, 2H), 6.90(m, 3H), 7.40(m, 1H).

Ir νmax (thin film): 3087, 2940, 1766(v.s.), 1649(v.s.), 1608, 1488, 1418, 1257, 1130, 994, 925, 981, 680 cm$^{-1}$.

EXAMPLE 20

Preparation of Compound No. 35 in Table 1

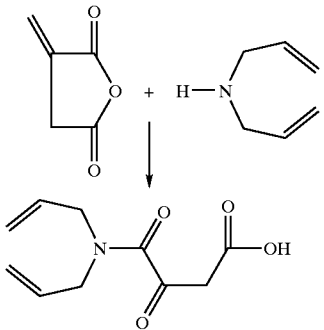

Itaconic anhydride (10.0 g, 0.09 mol) was placed in dry dichloromethane (150 cm3) and the mixture was cooled to −5° C. in a salt/ice bath. The diallylamine (9.72 g, 0.10 mol) in dry dichloromethane (50 cm$^3$) was added dropwise over 20 minutes, maintaining temperature >0° C. during addition. The mixture was stirred (during which a clear yellow solution was formed) for 1 hour. The solvent was removed in vacuo to leave a brown oil, 16.60 g, 89%

Ir νmax (thin film): 2400–3400, 1717(s), 1646(s), 1620(s), 1419, 1220, 995, 929, 842, 555 cm$^{-1}$.

$^1$HNMR (CDCl$_3$) δ: 3.35(s, 2H), 3.92(d, 2H), 4.10(d, 2H), 5.2(m, 4H), 5.70(s, 1H), 5.75(m, 2H), 6.35(s, 1H), 12.40 (s.v.br, 1H).

EXAMPLE 21

Preparation of Compound No. 38 in Table 1

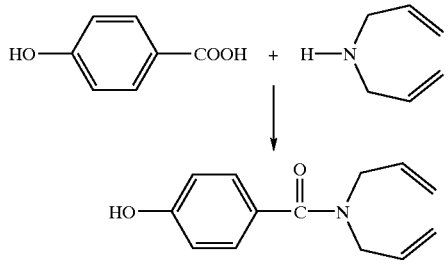

4-Hydroxybenzoic acid (10.0 g, 0.072 mol) and diallylamine (8.0 g, 0.082 mol) were dissolved in dichloromethane/tetrahydrofuran mixture (1:1) (100 cm$^3$). Dicyclohexylcarbodiimide (15.48 g, 0.075 mol) was added slowly and the mixture was stirred for 72 h. The dicyclohexylurea was removed by filtration (Whatman No. 1 filter paper) and solvents removed to leave a brown oil. The oil was dissolved in dry dichloromethane (100 cm$^3$) and the solution washed with 3M HCl solution (100 cm$^3$) and dried over MgSO$_4$. Removal of solvent left a white oily solid. Column chromatography (silica gel/EtOAc) followed by removal of solvent, gave after removal of solvent in vacuo a white powder, 14.6 g, 93%.

Ir νmax (KBr disc): 3098(br), 2932, 2809, 1640(w), 1573, 1447, 1281, 1241, 1174, 1112, 988, 936, 852, 748, 679, 636, 611, 575 cm$^{-1}$.

EXAMPLE 22

Preparation of Compound No. 39 in Table 1

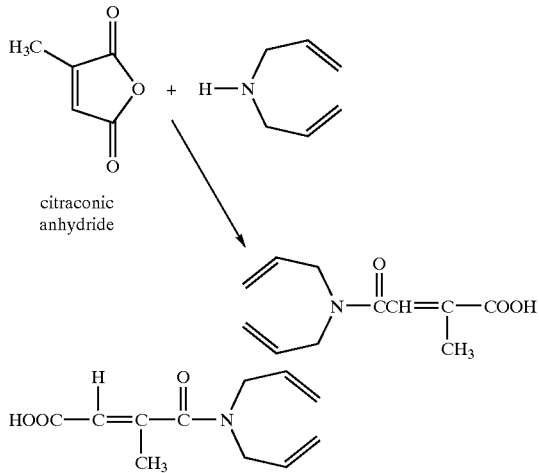

Citraconic anhydride (20.0 g, 0.178 mol) was dissolved in dry dichloromethane (300 cm3). Diallylamine (19.4 g, 0.20 mol) in dry dichloromethane (100 cm3) was added slowly dropwise over 45 minutes and stirring was continued for a further 1 h. The solvent was removed in vacuo to leave a brown oil, 34.85 g, 100%.

Ir νmax (thin film): 3600–2400, 1695(s), 1625(s), 1415, 1263, 1200, 1091, 997, 930, 798, 762, 661 cm$^{-1}$.

$^1$HNMR (CDCl$_3$) δ: 1.90(s), 3.40(d), 3.73(d), 3.80(d), 3.85(d), 3.92(d), 4.95–5.15(m), 5.18(d), 5.22(d), 5.29(d), 5.55–5.92(complex).

EXAMPLE 23

Preparation of Compound No. 41 in Table 1

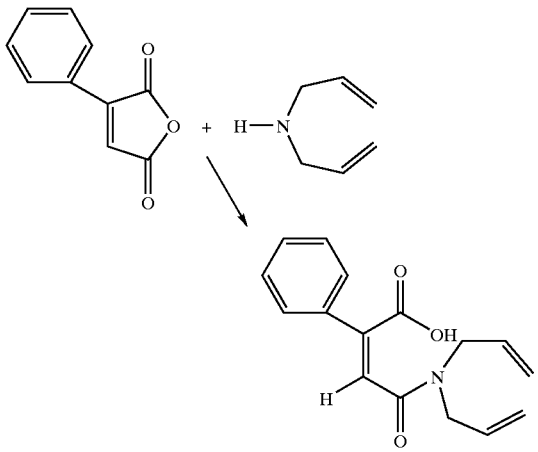

Phenylmaleic anhydride (5.0 g, 0.029 mol) was dissolved in dry dichloromethane (100 cm³ and stirred. Diallylamine (3.40 g, 0.035 mol) in dry dichloromethane (20 cm³) was added slowly dropwise over 10 minutes and stirring was continued for a further 1 h. The solvent was removed in vacuo and the residual brown oil thoroughly dried. 7.30 g, 94%. The oil solidified on standing.

Ir vmax (thin film): 3600–2500, 1625(s), 1700, 1420, 1363, 1200, 1091, 997, 930, 798,.762, 660 cm$^{-1}$.

$^1$HNMR (CDCl$_3$) δ: 3.60(d, 3.70(d), 4.10(d), 5.0(m), 5.20(m), 5.45(m), 5.90(m), 7.40(m), 7.55(m).

EXAMPLE 24

Preparation of Compound No. 42 in Table 1

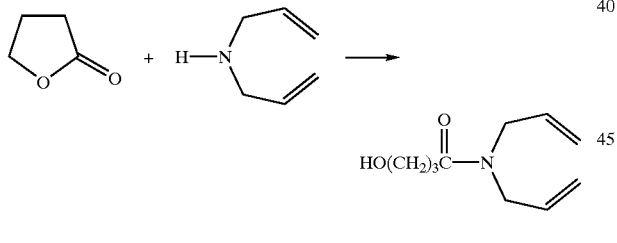

Gamma butyrolactone (5.00 g, 0.06 mol) and diallylamine (5.83 g, 0.06 mol) were mixed together (no solvent) and heated (60° C.) for 24 h. Thin layer chromatography (EtOAc) showed predominantly a new single product spot at ~Rf 0.25. The reaction mixture was dissolved in dry dichloromethane (100 cm³) and washed with 3N HCl (50 cm³), 3N K$_2$CO$_3$ solution (50 cm³) and then brine (50 cm³). Finally, the solution was dried over MgSO$_4$. The solvent was removed in vacuo and the residual brown oil purified using column chromatography (silica gel, ethyl acetate) to give after removal of solvent in vacuo, and thorough drying 7.4 g, 70%, of clear oil.

$^1$HNMR (CDCl$_3$) δ: 1.90(quin, 2H), 2.50(t, 2H), 3.55(s, 1H-OH), 3.66 (t, 2H), 3.90 (d, 2H), 4.00 (d, 2H), 5.15 (m, 4H), 5.75 (m, 2H).

Ir vmax (thin film): 3420 (br, s), 3088, 2935, 1630(s), 1417, 1359, 1283, 1239, 1138, 1063, 995, 927 cm$^{-1}$.

EXAMPLE 25

Preparation of Compound No. 43 in Table 1

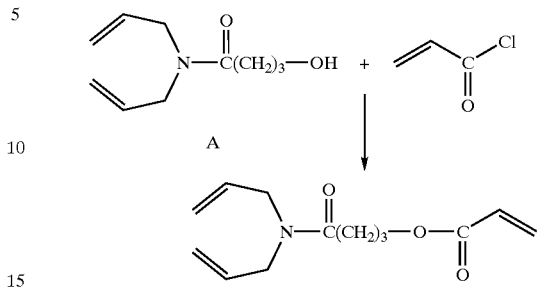

Amide A (10.0 g, 0.055 mol) was dissolved in dry dichloromethane (100 cm³) the mixture was cooled in an ice bath. Acryloyl chloride (4.95 g, 0.055 mol) in dry dichloromethane (20 cm³) was added dropwise over 30 minutes and the mixture was allowed to rise to room temperature. It was left stirring for 4 h. Thin layer chromatography (EtOAc) showed a new spot at ~Rf 0.6. The solvent was removed in vacuo and the product purified using column chromatography (EtOAc-40/60 petrol 1:1). Removal of solvent in vacuo gave a yellow oil 11.48 g, 89%.

Ir vmax (thin film): 2986, 1728(s), 1645(I), 1414, 1276, 1196, 1058, 992, 929, 813, 669 cm$^{-1}$.

$^1$HNMR (CDCl$_3$) δ: 2.10(m, 2H), 2.45(m, 2H), 3.90(d, 2H), 4.0(d, 2H), 4.2(t, 2H), 5.20(m, 2H), 5.75(m, 4H), 5.80(m, 1H), 6.15(m, 1H), 6.45(d, 1H).

EXAMPLE 26

Preparation of Compound No. 44 in Table 1

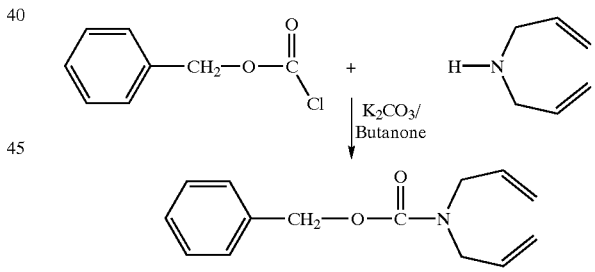

Benzyl chloroformate (10.0 g, 0.059 mol), diallylamine (5.85 g, 0.060 mol), potassium carbonate (10.0 g) in sieve dried butanone (100 cm³) were stirred together at ~reflux temperature for 3 h. Thin layer chromatography (ethyl aetate) showed a new spot at ~Rf 0.5 and no evidence of diallylamine. The reaction mixture was filtered (Whatman No. 1 filter paper) and solvent removed in vacuo to leave a brown oil. The oil was purified using column chromatography (silica gel with ethyl acetate as eluent). Removal of solvent in vacuo left a clear yellow oil, 10.34 g, 77%.

Ir vmax (thin film): 2987, 1708(s), 1460, 1415, 1368, 1294, 1243, 1153, 1096, 995, 926, 769, 699 cm$^{-1}$.

$^1$HNMR (CDCl$_3$) δ: 3.85(d, 4H), 5.11(m, 4H), 5.14(s, 2H), 5.75(m, 2H). 7.30(m, 5H).

EXAMPLE 27

Preparation of Compound No. 45 in Table 1

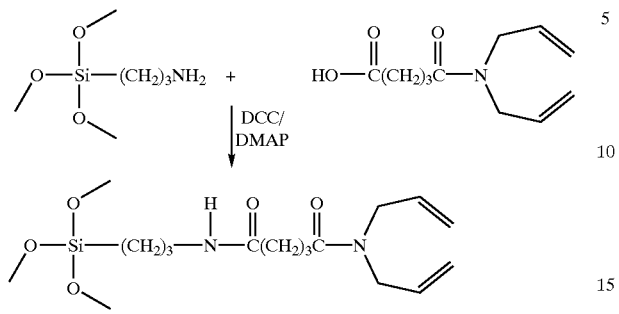

3-aminopropyltrimethoxysilane (10.0 g, 0.056 mol), 4-diallylamidobutyric Acid (11.8 g, 0.056 mol), dicyclohexylcarbodiimide (11.55 g, 0.056 mol) and 4-dimethylaminopyridine (0.5 g) were stirred at room temperature in dry dichloromethane for 72 h. The dicyclohexylurea was removed by filtration (Whatman No. 1 filter paper) and solvent removed to leave a yellow oil. The oil was passed through a short column of neutral aluminium followed by ethyl acetate (500 cm$^3$). Removal of solvent left a clear colourless oil 16.8 g, 80%.

Ir vmax (thin film): 3314, 2940, 2120, 1650(s), 1547, 1417, 1229, 1086, 994, 927, 808, 754, 666 cm$^{-1}$.

$^1$HNMR (CDCl$_3$) δ: 0.65(t, 2H), 1.95(quin, 2H), 2.25(t, 2H), 2.40(t, 2H), 3.20(quin, 2H), 3.55(s, 9H), 3.90(d, 2H), 4.0(d, 2H), 5.10(m, 4H), 5.75(m, 2H), 6.5(d, 2H).

EXAMPLE 28

Preparation of Compound No. 46 in Table 1

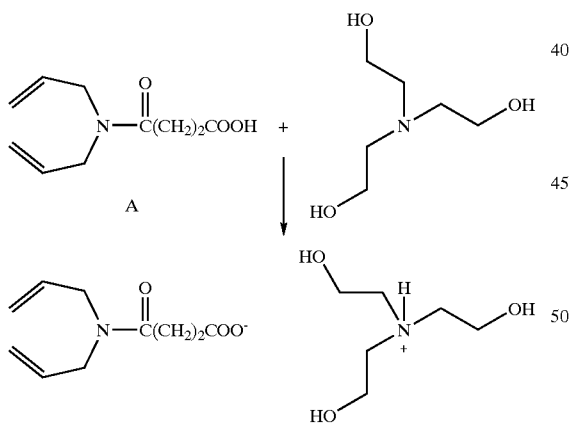

Amide A (5.0 g, 0.0254 mol) and triethanolamine (3.78, 0.0254 mol) were dissolved in dry dichloromethane (100 cm$^3$) and stirred at room temperature for 1 hr. The solvent was removed in vacuo to leave a pale yellow oil (8.78 g, 100%) which was not purified since both of the starting materials were 98–100% pure.

$^1$HNMR (CDCl$_3$) δ: 2.55(m, 2H), 2.60(m, 2H), 2.98(t, 6H), 3.75(t, 6H), 3.95(m, 4H), 5.15(m, 1H), 5.76(m, 2H), 6.32(s, br, 4H).

Ir vmax (thin film): 3363 (s), 3156, 2936, 1639(s), 1579 (s), 1409, 1249, 1080, 1032, 1003,. 918, 563 cm$^{-1}$.

EXAMPLE 29

Preparation of Compound No. 47 in Table 1

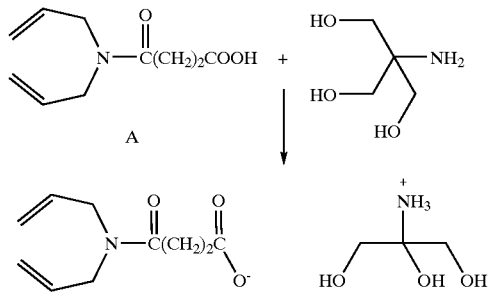

Amide A (5.0 g, 0.0254 mol) and tris(hydroxymethyl) aminoethane (3.08 g, 0.0254 mol) were placed together in dry dichloromethane (100 cm3) and the combination stirred for 1 h at room temperature. The solvent was removed in vacuo to leave a pale yellow oil which was not further purified since both starting materials were 98–100% pure. Yield 8.08 g, 100%.

$^1$HNMR (CDCl$_3$) δ: 2.40(s, br, 2H), 2.60(s, br, 2H), 3.75(s, br, 8H), 3.95(s, br, 2H), 5.15(m, 4H), 5.70(m, 2H), 6.85(s, br, 6H, —OH$_1$+NH)

Ir vmax (thin film): 3392, 1561, 1463, 1407, 1221, 1190, 1063, 933, 565 cm$^{-1}$.

EXAMPLE 30

Preparation of Compound No. 48 in Table 1

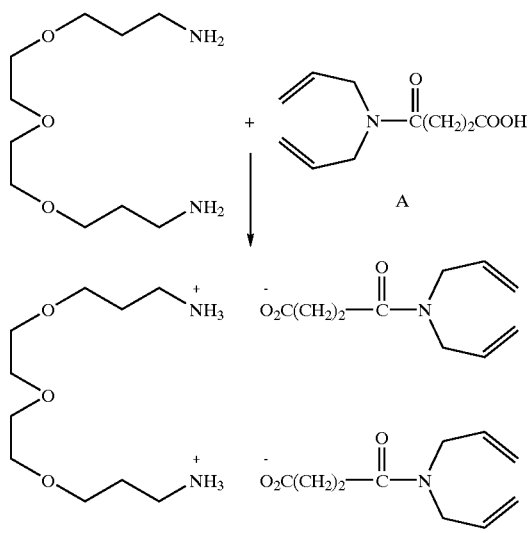

4,7,10-Trioxa-1,13-tridecanediamine (5.0 g, 0.0227 mol) and amide A (8.94 g, 0.045 mol) were dissolved in dry dichloromethane (100 cm$^3$) and stirred at room temperature for 1 hour. The solvent was removed in vacuo to leave a pale yellow oil which was not further purified since both starting materials were 98–100% pure. Yield 13.94 g, 100%.

$^1$HNMR (CDCl$_3$) δ: 1.93(t, 4H), 2.45(t, 4H), 2.60(t, 4H), 3.00(t, 4H), 3.60(m, 12H, —CH$_2$ NH$_3$), 3.95(m, 8H), 5.17 (m, 8H), 5.77(m, 4H), 7.60(s, br, 6H).

Ir vmax (thin film): 2876(s), 1647(s), 1412, 1243, 1117, 997, 929, 870, 558 cm$^{-1}$.

EXAMPLE 31

Preparation of Compound No. 54 in Table 2

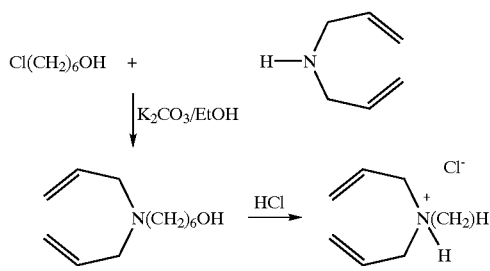

6-Chlorohexan-1-ol (10.0 g, 0.073 mol), diallylamine (7.30 g, 0.075 mol) and potassium carbonate (10.37 g, 0.075 mol) were placed in ethanol (150 cm$^3$) and refluxed for 48 h. The solvent was removed in vacuo to leave a brown oil. The oil was dissolved in dichloromethane (150 cm$^3$) and the solution was washed in brine (100 cm$^3$), then dried over MgSO$_4$. The solvent was removed in vacuo and the residual brown oil purified using column chromatography (silica gel—ethyl acetate). Removal of solvent in vacuo gave a yellow oil, 14.7 g, 99%.

$^1$HNMR (CDCl$_3$) δ: 1.40(m, 2H), 1.50(quin, 2H),; 1.55 (quin, 2H), 2.45(t, 2H), 2.65(s, 1H), 3.10(d, complex, 4H), 3.55(t, 2H), 3.65(quartet, 2H), 5.10(m, 4H), 5.80(m, 2H).

Ir vmax (thin film): 3369(s), 2964, 2934, 1517, 1459, 1374, 1300, 1243, 1106, 1047, 1018, 826, 770 cm$^{-1}$.

Salt formation was achieved by quarternerization using methanolic hydrochloric acid (6N).

EXAMPLE 32

Preparation of Compound No. 58 in Table 2

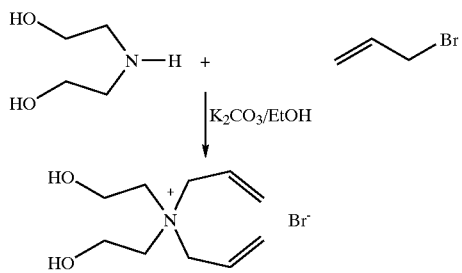

Diethanolamine (10.0 g, 0.095 mol), allyl bromide (24.2 g, 0.20 mol) and potassium carbonate (34.5 g, 0.25 mol) were placed in ethanol (150 cm$^3$) and the mixture was warmed to 65–70° C. with stirring and kept at this temperature for 15 h. Solids were removed by filtration and the solvent removed in vacuo to leave a yellow oil, 21.7 g, 86%.

Ir vmax (thin film): 3600–3100(s), 2980, 1647, 1457, 1366, 1090, 955, 754 cm$^{-1}$.

$^1$HNMR (CDCl$_3$) δ: 3.62(s, 2H), 3.78(d, 2H), 3.98(s, 2H), 4.10(m, 4H), 4.24(m, 4H), 5.24(m, 4H), 6.10 (m, 2H).

EXAMPLE 33

Preparation of Compound No. 59 in Table 2

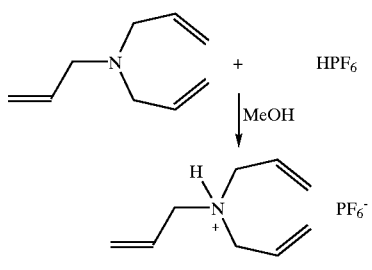

Triallylamine (20.0 g ) was dissolved in methanol and stirred at room temperature. 6N hexafluorophosphoric acid in methanol (from 65% solution in H$_2$O ) was added to pH 2.0 and the pink solution was left stirring for 15 minutes The solvents (MeOH and H$_2$O) were removed in vacuo to leave a pink coloured oil. The oil was re-dissolved in dry dichloromethane and the solution was dried over MgSO$_4$. It was then filtered (Whatman No. 1 filter paper+'Hyflo"). Removal of solvent in vacuo gave a clear, pink coloured oil, 35.4 g 85%.

Ir vmax (thin film): 2997, 2543, 1459, 1429, 1289, 1244, 1143, 1056, 997, 953, 8.41(s), 756, 661 cm$^{-1}$.

$^1$HNMR (CDCl$_3$) δ: 3.65(s, 6H), 5.55(m, 6H), 6.0(m, 3H), 10.55(s, br, 1H).

EXAMPLE 34

Preparation of Compound No. 60 in Table 2

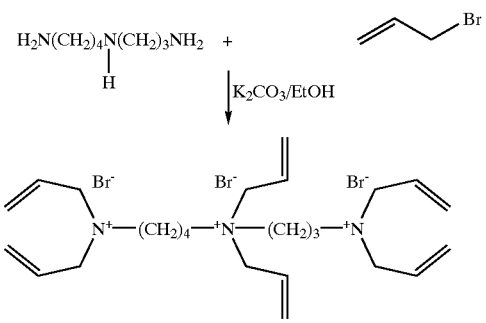

Spermidine (5.0 g, 0.035 mol), allyl bromide (34.0 g, 0.28 mol), potassium carbonate (35.0 g ) and ethanol (100 cm$^3$)were refluxed for 6 h at 60° C. The solvent and excess allyl bromide were removed in vacuo to leave a brown oil, 21.0 g, 84%.

$^1$HNMR (CD$_3$OD) δ: 1.95(m, 4H), 2.55 (quin, 2H), 3.45 (m, 8H), 4.0(d, 8H), 4.15(d, 8H), 5.75(m, 16H), 6.20(m, 8H).

Ir vmax (thin film): 2934, 2458, 1644, 1472, 1427, 1368, 1246, 995, 953, 848, 749, 662 cm$^{-1}$.

EXAMPLE 35

Preparation of Compound No. 62 in Table 3

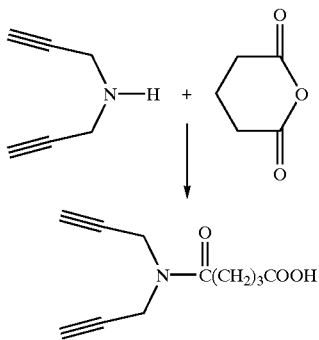

Glutaric anhydride (3.68 g, 0.032 mol) was placed in dry dichloromethane (100 cm³) but did not dissolve. Dipropargylamine (3.00 g, 0.032 mol) in dry dichloromethane (25 m³) was added slowly dropwise with a rise in temperature due to an exothermic reaction. As addition of the dipropargylamine proceeded, the glutaric anhydride became less evident until a clear yellow reaction mixture was formed. This was left stirring for a further 1 h. The solution was washed in (i) dil (1N) (50 ml) HCl solution, (ii) NaHCO₃ solution (1N) (50 ml), water (50 ml), then dried over MgSO₄ to leave an orange coloured oil, 6.38 g, 96%.

Ir vmax (thin film): 3300, 2940, 2863, 2130, 1730(s), 1660(s), 1420, 1345, 1211, 1040, 956 cm$^{-1}$.

EXAMPLE 36

Preparation of Compound No. 63 in Table 3

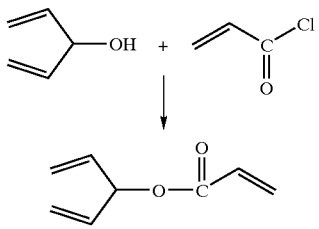

1,4-Pentadien-3-ol (5.0 g, 0.060 mol) and acryloyl chloride (5.43 g, 0.060 mol) were dissolved in dry acetone. Potassium carbonate (10 g) was added and the mixture was stirred at reflux for 15 h. The solids were removed by filtration (Whatman No. 1 filter paper) and the solvent removed in vacuo to leave a yellow oil. Chromatography using flash silica gel with ethyl acetate as the eluent gave, after thorough drying in vacuo, etc. 6.43 g, 78% of pale yellow oil.

Ir vmax (thin film): 2935, 1736(s), 1653, 1618, 1411, 1186, 1090, 989, 931, 810 cm$^{-1}$.

¹HNMR (CDCl₃) δ: 5.10–5.45(m, 5H), 5.70–5.95(m, 3H), 6.20(m, 1H), 6.45(m, 1H).

What is claimed is:

1. A method of adhering or sealing surfaces, said method comprising (1) applying to at least one surface, a compound of formula (I)

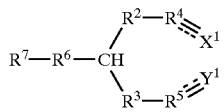

where;

R² and R³ are independently selected from $(CR^{8'}R^8)_n$, or $CR^9R^{10}$, $-(CR^{8'}R^8CR^9R^{10})-$ or $-(CR^9R^{10}CR^{8'}R^8)-$ where n is 0, 1 or 2, $R^{8'}$ and $R^8$ are independently selected from hydrogen or alkyl, and either one of $R^9$ or $R^{10}$ is hydrogen and the other is an electron withdrawing group, or $R^9$ and $R^{10}$ together form an electron withdrawing group, R⁴ and R⁵ are independently selected from C, CH or CR¹¹ where R¹¹ is an electron withdrawing group, R⁶ is a bond or an electron withdrawing group; and R⁷ is selected from hydrogen, an optionally substituted hydrocarbyl group, a perhaloalkyl group or a functional group;

the dotted lines indicate the presence or absence of a bond, and X¹ is CX²X³ where the dotted line bond is absent and CX² where the dotted line bond is present, Y¹ is CY²Y³ where the dotted line bond is absent and CY² where the dotted line bond is present, and X², X₃, Y² and Y³ are independently selected from hydrogen or fluorine;

provided that at least one of (a) R⁶ or (b) R² and R³ or (c) R⁴ and R⁵ includes an electron withdrawing group;

and optionally, a polymerisation initiator, and (2) allowing the compound of formula (I) to polymerise in contact with a second surface such that the said surfaces are adhered or sealed.

2. A method according to claim 1 wherein the compound of formula (I) is a compound of formula (IA)

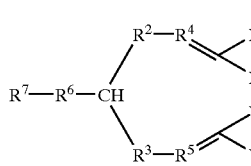

(IA)

where R², R³, R⁴, R⁵, R⁶, R⁷, X², X³, Y² and Y³ are as defined in claim 1.

3. A method according to claim 1 wherein the compound of formula (I) is polymerised under the influence of radiation or an electron beam, or by reaction with a chemical initiator.

4. A method according to claim 3 wherein the compound of formula (I) is polymerisable under the influence of ultra violet or thermal radiation.

5. A method according to claim 4 wherein the compound of formula (I) is curable under the influence of ultraviolet light.

6. A method according to claim 5 which comprises a polymerization initiator which is a photoinitiator.

7. A method according to claim 1 wherein R⁶ is an electron withdrawing group.

8. A method according to claim 7 wherein in the compound of formula (I), R² and R³ are $(CR^{8'}R^8)_n$ and R⁴ and R⁵ are CH.

9. A method according to claim 1 where R⁶ is —C(O)O— or —OC(O)— or —S(O)₂—.

10. A method according to claim 9 where R⁶ is —C(O)O— or —OC(O)—.

11. A method according to claim 1 where $R^2$ and $R^3$ includes an electron withdrawing group.

12. A method according to claim 11 where at least one of $R^2$ or $R^3$ include electron withdrawing groups $R^9$ and $R^{10}$.

13. A method according to claim 12 wherein $R^9$ and $R^{10}$ together form an oxo group.

14. A method according to claim 1 wherein $R^7$ comprises a hydrocarbyl group optionally substituted by a functional group.

15. A method according to claim 1 wherein $R^7$ includes an unsaturated moiety.

16. A method according to claim 15 wherein the unsaturated moiety is an aryl or alkenyl group, or a carbonyl substituent.

17. A method according to claim 14 wherein $R^7$ is an optionally substituted alkyl, alkenyl, alkynyl or aryl group.

18. A method according to claim 17 wherein $R^7$ is substituted by halogen, carboxy or salts thereof or acyloxy.

19. A method according to claim 14 where $R^7$ is a perhaloalkyl group which comprises from 1 to 3 carbon atoms.

20. A method according to claim 19 where $R^7$ is a perhalomethyl group.

21. A method according to claim 14 where $R^7$ is a dialkenyl substituted amide.

22. An article which includes at least two surfaces which are adhered together by means of a compound of formula (I) as defined in claim 1 which has been polymerised.

23. An article according to claim 22 wherein the surfaces comprise glass or metal surfaces or a mixture of these.

24. An article according to claim 22 wherein the polymerised compound of formula (I) provides an electrically conducting layer.

25. An adhesive which comprises a compound of formula (I) as defined in claim 1.

26. A biomedical adhesive which comprises a biocompatible compound of formula (I) as defined in claim 1.

27. A sealant which comprises a compound of formula (I) as defined in claim 1.

28. A sealant which comprises a biocompatible compound of formula (I) as defined in claim 1.

* * * * *